United States Patent [19]
Arpa et al.

[11] Patent Number: 5,374,272
[45] Date of Patent: Dec. 20, 1994

[54] APPARATUS AND METHOD FOR MECHANICALLY DILATING THE PUPIL OF AN EYE

[75] Inventors: Paolo Arpa, Milan, Italy; Gholam A. Peyman; Stephen A. Updegraff, both of New Orleans, La.

[73] Assignee: Vitrophage, Inc., Lyons, Ill.

[21] Appl. No.: 84,556

[22] Filed: Jun. 29, 1993

[51] Int. Cl.⁵ .............................. A61B 17/02
[52] U.S. Cl. .................... 606/107; 128/20; 606/191
[58] Field of Search ............... 606/107, 166, 191, 198; 128/20

[56] References Cited

U.S. PATENT DOCUMENTS

| | | | |
|---|---|---|---|
| 3,490,455 | 1/1970 | Illig | 128/20 |
| 4,037,589 | 7/1977 | McReynolds | 606/107 |
| 4,387,706 | 6/1983 | Glass | 606/107 |
| 4,782,820 | 11/1988 | Woods | 128/20 |
| 5,071,421 | 12/1991 | Stahl | 606/107 |
| 5,159,921 | 11/1992 | Hoover | 128/20 |
| 5,163,419 | 11/1992 | Goldman | 606/107 |
| 5,174,279 | 12/1992 | Cobo et al. | 606/107 |
| 5,267,553 | 12/1993 | Graether | 128/20 |
| 5,299,564 | 4/1994 | Sabatino | 128/20 |
| 5,318,011 | 6/1994 | Federman et al. | 606/107 |
| 5,322,054 | 6/1994 | Graether | 128/20 |

FOREIGN PATENT DOCUMENTS

| | | | |
|---|---|---|---|
| 114051 | 3/1918 | United Kingdom | 128/20 |
| 990220 | 1/1983 | U.S.S.R. | 128/20 |
| 1258405 | 9/1986 | U.S.S.R. | 606/191 |
| 1500292 | 8/1989 | U.S.S.R. | 606/107 |

OTHER PUBLICATIONS

Arpa, Paolo, "A New Device for Pupillary Dilatation in Vitreous Surgery", RETINA, Jul.-Sep. 1992, vol. 12, No. 3 Supplement, ©J. B. Lippincott Co.

Primary Examiner—Ralph A. Lewis
Attorney, Agent, or Firm—Wood, Herron & Evans

[57] ABSTRACT

A pupillary dilation and protection device is disclosed comprising an elastomeric ring made from biocompatible material having a groove formed therein for receiving and protecting the pupillary rim and iris, whereby, when the ring is inserted into the pupil of an eye of a patient, it mechanically dilates the pupil.

10 Claims, 2 Drawing Sheets

APPARATUS AND METHOD FOR MECHANICALLY DILATING THE PUPIL OF AN EYE

FIELD OF THE INVENTION

The present invention relates generally to devices and methods for dilating and protecting pupils and more particularly to a flexible, grooved ring inserted into the eye to protect and mechanically dilate a pupil without the problems associated with demolitive or conservative measures.

BACKGROUND OF THE INVENTION

Good pupillary dilation is beneficial for numerous medical procedures, such as, vitreoretinal surgery, anterior segment surgery, and phacoemulsification to name but a few. If an operation is performed through a small pupil, it can lead to severe trauma to the iris posterior pigment epithelium and damage to the iris sphincter resulting in permanent iris distortion and disabling glare. Additionally, poor visualization of the procedure may lead to small capsuleorhexis (which may result in a contraction syndrome requiring a subsequent lens explantation), zonar dehiscene, capsular rupture, vitreous loss leading to permanent decreased vision, lens material in the posterior segment requiring retinal surgery for removal, retained cortical material and prolonged surgical times. Each of these complications is potentially avoidable by fixed dilation of the pupil. Although mydriatic drugs are preferred for dilating the pupils, in many patients these drugs are ineffective because of the patient's ocular pathologic characteristics (i.e., aphakia, diabetes, phlogistic diseases, etc.). Several solutions, both demolitive and conservative, have been attempted.

The demolitive measures, such as irridectomies, sphincterotomies, and removal of the pupillary sphincter, for example, all suffer from the same shortcomings; each can potentially permanently deprive the patient of normal pupillary kinetics. For example, sphincterectomies may lead to permanent dilation and disabling glare, whereas preplaced sutures are tedious to place and may induce bleeding.

Among the conservative measures, pupillary stretching is most popular. However, this technique cannot be used on phakic eyes. Further, it is time consuming to implement and tends to stress the iris sphincter at individual points, thereby causing irregular distortions in the iris, sphincter tears, radial streaks of iris atrophy.

Thus, there has been a considerable need for a procedure for reliably and easily dilating the of a patient while at the same time protecting the iris from damage.

SUMMARY OF THE INVENTION

The present invention provides a device adapted to easily, safely and reliably engage and mechanically dilate the pupillary rim of an iris. To this end, and in accordance with the principles of the present invention, a ring made of biocompatible elastic material is provided having a generally C-shaped circumferential groove formed therein adapted to receive and protect the pupillary rim. This groove divides the ring into a superior flange, a connecting inner wall and an inferior flange.

To dilate the pupil, the flexible ring is introduced to the pupil in a compressed state. Greater flexibility, which assists in compressing the ring without adversely affecting its stability, is provided by a series of spaced slits along the perimeter of the inferior and superior flanges. The pupillary rim is then engaged in the inferior flange and the ring is permitted to return to its undeformed shape. As the ring expands radially outward, the force against the pupillary rim urges it to enter the groove until it is fully received therein. Depending upon the size of the ring employed, the expansion will continue and the force of the inner wall against the pupillary rim will force the pupillary rim to dilate until the ring has resumed its fully undeformed shape. Because the ring distributes the force equally over the entire pupillary rim, the rim is not damaged and the pupil resumes its undilated size and shape upon removal of the ring.

The flexible ring could be formed from "Silastic" tubing (Dow Corning, Midland, Mich.) by removing a strip of the wall for the entire length of the tube and forming the tube into a ring. However, as described fully in Retina: "A New Device for Pupillary Dilation in Vitreous Surgery" by P. Arpa, M.D., 12: S87–S89 (1992), a molded ring is preferred because it eliminates the unevenness of the ring surface experienced with tubing.

Additionally, it has been found to be beneficial for the inferior flange to have a larger radial dimension than the superior flange, which can be achieved through molding of the ring. Such a structure aids in guiding the pupillary rim into the groove during insertion of the ring. Further, it serves to reduce posterior pigment epithelium trauma and, during phacoemulsification, iris capture.

By virtue of the foregoing, there is thus provided a device and method for quickly, easily and safely dilating the pupil of an eye. These and other objects and advantages of the present invention shall be apparent from the accompanying drawings and the descriptions thereof.

BRIEF DESCRIPTION OF THE DRAWINGS

The accompanying drawings, which are incorporated in and constitute a part of this specification, illustrate embodiments of the invention and, together with a general description of the invention given below, serve to explain the principles of the invention.

DETAILED DESCRIPTION OF THE DRAWINGS

Figure 1:
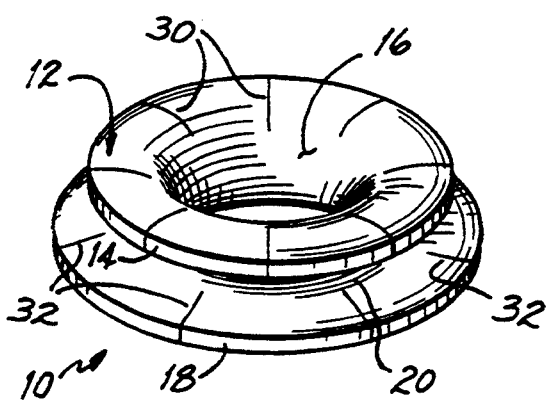
FIG. 1 is a top perspective view of a pupillary dilation device in accordance with the principles of the present invention.
Figure 2:
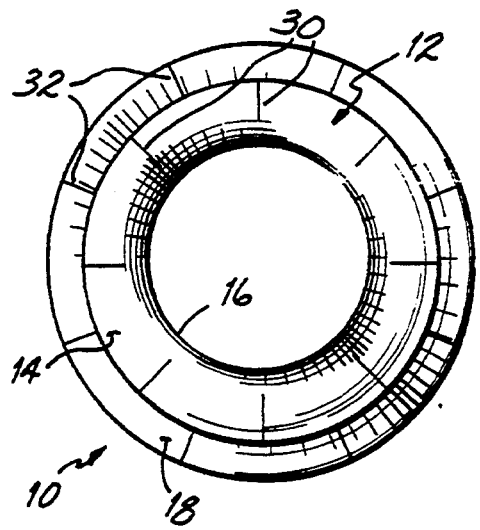
FIG. 2 is a top view of the pupillary dilation device of FIG. 1.
Figure 3:
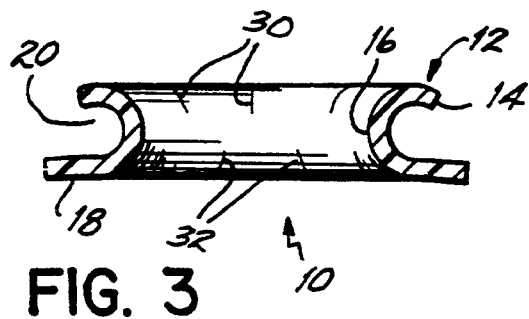
FIG. 3 is a cross-sectional view of the pupillary dilation device taken along line 3—3 of FIG. 2.
Figure 5:
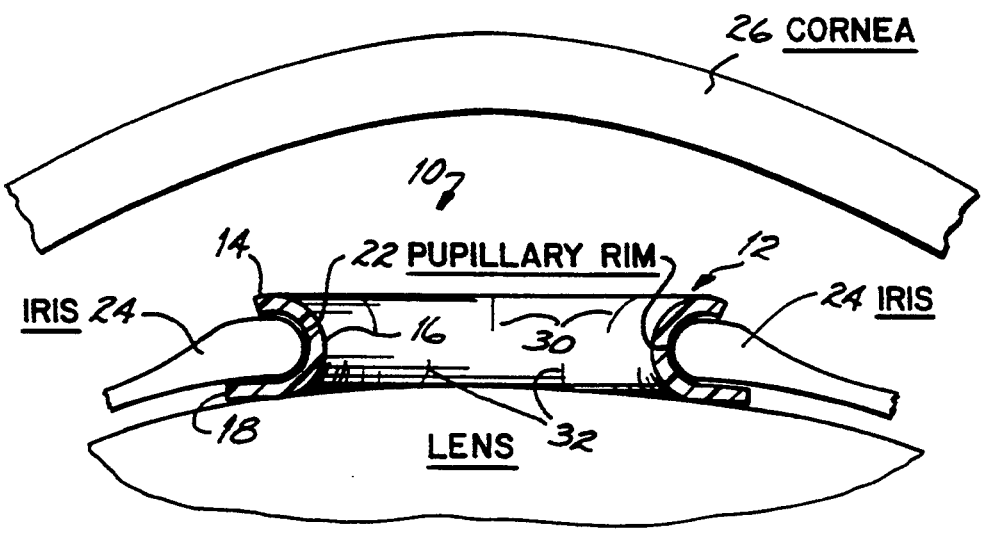
FIG. 5 is a fragmentary view of a human eye illustrating the use of the pupillary dilation device of FIG. 1.
Figure 4:
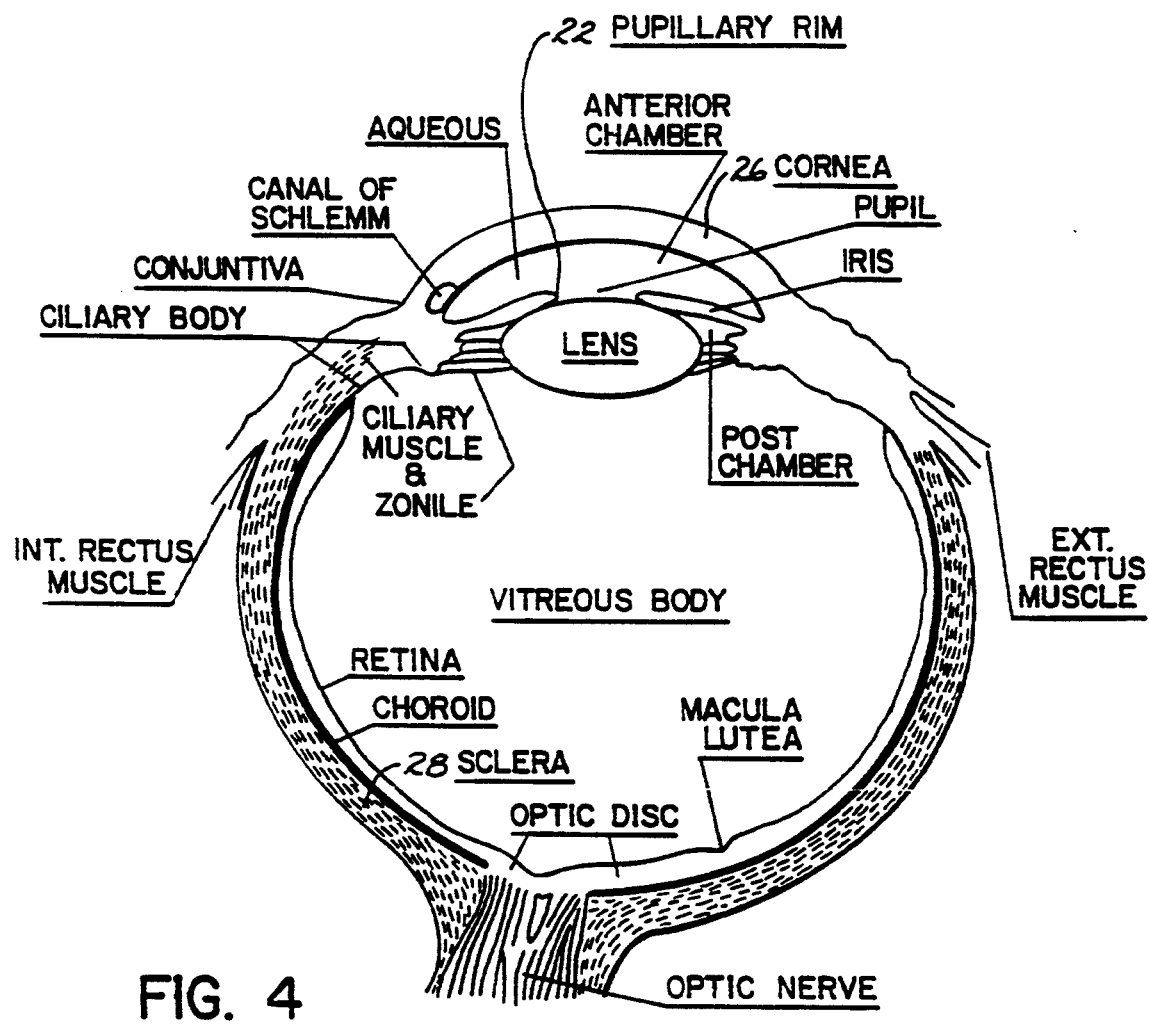
FIG. 4 is an anatomical illustration of the human eye.

With reference to FIGS. 1-3, there is shown a pupillary dilation device 10 comprising an annular ring 12 having a generally C-shaped cross-section thereby dividing annular ring 12 into a superior flange 14, a connecting inner wall 16 and an inferior flange 18. Together, superior flange 14, inner wall 16 and inferior flange 18 define an annular groove 20 for receiving, engaging, protecting and dilating the pupillary rim 22 and iris 24 of the eye (FIGS. 4 and 5). Finally, superior flange 14 and inferior flange 18 may include slits 30, 32 formed therein for a purpose to be described hereinafter.

Because dilation device 10 is to be used for mechanically dilating pupillary rim 22 and iris 24 of an eye, a biocompatible material should be used in its construction. Further, the material should be both flexible, to aid in insertion, and elastic, to provide the dilatory force. "Elastic", as the term is used herein, means the property of recovering to the original shape after deforming forces are removed. One elastic material possessing all of the characteristics is an organosilicone polymer sold under the name "Silastic" by Dow Corning. However, other suitable elastic or elastomeric materials exist that may be used including butyl rubbers, ethylene propylene diene terpolymer (EPDM), polysulfide rubber, silicone rubber, neoprene (polychloroprene), chlorsulfonated polyethylene, acrylonitrile-butadiene copolymer (nitrile rubber), styrene butadiene copolymer, acrylonitrile butadiene, copolymer-polyvinyl chloride polymer blends, polyisobutylene, polyepichlorohydrin, natural and synthetic polyisoprene, polyvinyl chloride-polybutadiene rubber, polyurethanes, fluorocarbon elastomers such as vinylidene, fluoride-chlorobifluorethylene copolymers, vinylidene-fluoride-hexafluorethylene copolymers, and fluoroacrylate elastomers as well as others.

With reference to FIGS. 4 and 5, in use, a compressed or deformed dilation device 10 is inserted through a small pocket incision in either the cornea 26 or sclera 28 with forceps or other appropriate instrument. For example, McPherson forceps, which are well known in the art, are particularly useful in the insertion process because they have two fine jaws that can be inserted into groove 20 on opposite sides of annular ring 12, thus permitting ring 12 to be compressed for insertion through the incision. To improve the flexibility of ring 12, without adversely affecting its stability, slits 30, 32 may be formed respectively along the perimeter of superior flange 14 and inferior flange 18. These slits are staggered along the perimeter at about 45° increments, although any spacing and number of slits may be used. Further, it is preferable that the position of the superior flange slits 30 be staggered from that of the inferior flange slits 32. This reduces the possibility of tearing of the ring 12 at the slits during the insertion process. Slits 30, 32 preferably are formed through superior flange 14 and inferior flange 18, and extend from the perimeter of flanges 14, 18 to about the inner wall 16 of ring 12. However, it will be readily appreciated that the length that slits 30, 32 extend into ring 12 can vary and still fall within the principles of the present invention.

After insertion through the incision, the inferior flange 18 is positioned to engage the pupillary rim 22. Dilation device 10 is then carefully released and permitted to return to its undeformed shape. With guidance from the user, expansion of ring 12 progressively urges the remainder of pupillary rim 22 into groove 20 and partially surrounds the iris 24. Further expansion of ring 12 uniformly dilates the pupillary rim 22 and iris 24 to the undeformed size of dilation device 10.

Thus, the extent of the dilation produced by dilation device 10 is dependent upon the inner diameter of annular ring 12. Because the desired size of the pupil opening may vary with the medical procedure to be performed, it is beneficial to have dilation devices having a range of inner diameter sizes from about 5 mm to about 9 mm. This range encompasses the dilation sizes typically used during ophthalmological procedures. However, it will be appreciated by those skilled in the art that diameter sizes outside of this range may be used and still fall within the principles of the present invention.

To extract dilation device 10, vitreous forceps, or a comparable instrument, are used after a portion of ring 12 is released from the pupillary rim 22 with a subtile flat spatula. Particular care must be exercised during this procedure to avoid engaging the pupillary rim 22 with the spatula, which could result in damage to the iris sphincter. This is particularly likely if dilation device 10 is removed via pars plana, rather than through the incision used for insertion, because the spatula is hidden from view behind the iris 24.

Following extraction of dilation device 10, the dilated pupils quickly return to their original undilated round shape. Because groove 20 distributes the dilation force uniformly across the pupillary rim 22, use of dilation device rarely results in sphincter tears or iris atrophy. Further, dilation device 10 is effective with both phakic and aphakic patients.

Groove 20 can be formed by removing a portion of the wall of silastic tubing and forming the tubing into a ring as described in Retina: "A new Device for Pupillary Dilation in Vitreous Surgery" by P. Arpa, M.D., 12: S89 (1992), which is incorporated herein by reference. However, it is preferred that dilation device 10 be directly molded for two particular reasons. First, molding of dilation device 10 eliminates the irregularities associated with tubing, particularly at the joint where the two ends of the tubing are connected. Second, it has been found to be highly desirable for inferior flange 18 to have a larger radial dimension than superior flange 14, which can be easily controlled through molding. A larger inferior flange aids in guiding the iris 24 into groove 20 during the insertion process. It also reduces posterior pigment epithelium trauma and iris capture, particularly during phacoemulsification. The preferred radial dimension of inferior flange 18 is from about 0.5 mm to about 4.0 mm, while that of superior flange 14 is from about 0.5 mm to about 2.0 mm. Again, it will be recognized by those skilled in the art that these are only preferred dimensions and flange sizes outside of these ranges fall within the principles of the present invention.

Finally, dilation device 10 should have a groove width of about 0.1 mm to about 0.3 mm and an overall width of about 0.5 mm to about 1.0 mm. If dilation device 10 is wider than this size, it may be difficult to insert the device into the pupil. Alternatively, if it is smaller than this size, groove 20 may be unable to accommodate the pupillary rim 22 without undue damage thereto.

The dilation device 10 as disclosed has many applications. It is particularly useful in providing safe and reliable dilation of the pupil, thereby providing good visualization of the posterior pole and retina periphery during vitreoretinal surgery. However, it is also useful for dilating pupils that are unresponsive to pharmacologic agents, for preventing pupillary constriction during routine phacoemulsification, in cases where emergency dilation is needed such as intraoperative pupillary miosis during phacoemulsification and during "open sky" triple procedures to aid in visualization of lens removal, implantation and/or vitroectomy.

By virtue of the foregoing, there is thus provided a pupillary dilation and protection device that may easily and quickly be inserted and removed, and that safely and reliably dilates the pupil without the complications experienced with the prior art demolitive or conservative measures. While the present invention has been illustrated by description of two embodiments, it is not the intention of the applicant to restrict or limit the scope of the appended claims to such detail. For example, dilation device 10 could be formed without slits 30, 32 and still fall within the principles of the present invention. Additional advantages will readily appear to those skilled in the art; thus, the invention is not limited to the specific details, apparatus or method shown and described.

What is claimed is:

1. A pupillary dilation and protection device comprising:
    a biocompatible elastic ring having a radially outwardly extending annular inferior flange, a radially outwardly extending annular superior flange and an interconnecting annular inner wall forming a generally C-shaped annular groove;
    said inferior flange having a radial dimension larger than said superior flange to aid in engaging and protecting the pupillary rim;
    whereby when said ring is inserted into the pupil of an eye, said groove engages and mechanically dilates the pupillary rim.

2. The pupillary dilation and protection device of claim 1 wherein said biocompatible elastic ring is made from an organosilicone polymer.

3. The pupillary dilation device of claim 1 further comprising a plurality of slits formed along the perimeters of said superior flange and said inferior flange.

4. The pupillary dilation and protection device of claim 1 wherein the inner diameter of said ring is from about 5 mm to about 9 mm.

5. The pupillary dilation and protection device of claim 1 wherein the outer diameter of said ring is from about 6 mm to about 10 mm.

6. The pupillary dilation and protection device of claim 1 wherein said inferior flange has a radial dimension from about 0.5 mm to about 4.0 mm.

7. The pupillary dilation and protection device of claim 1 wherein said superior flange has a radial dimension from about 0.5 mm to about 2.0 mm.

8. The pupillary dilation and protection device of claim 1 wherein said ring has a width from about 0.5 mm to about 1.0 mm.

9. The pupillary dilation and protection device of claim 1 wherein said annular C-shaped groove has an internal diameter of about 0.1 mm to about 0.3 mm.

10. A method of mechanically dilating the pupil of an eye comprising:
    providing a biocompatible elastic ring having an undeformed shape and a radially outwardly extending annular inferior flange, a radially outwardly extending annular superior flange having a smaller radial dimension than the radial dimension of said inferior flange and an interconnecting annular inner wall defining a circumferential groove adapted to receive the pupillary rim of an eye;
    making an incision in the corneal or scleral pocket of the eye;
    compressing said ring;
    inserting said compressed ring through the incision;
    placing said compressed ring into the pupil of the eye;
    engaging the pupillary rim with said groove;
    releasing said compressed ring and permitting said ring to resume its undeformed shape thereby mechanically dilating the pupil and protecting said pupillary rim.

* * * * *

UNITED STATES PATENT AND TRADEMARK OFFICE
CERTIFICATE OF CORRECTION

PATENT NO. : 5,374,272
DATED : 12/20/94
INVENTOR(S) : Paolo Arpa, Gholam A. Peyman and Stephen A. Updegraff It is certified that error appears in the above-indentified patent and that said Letters Patent is hereby corrected as shown below:

Column 1, Line 51, "dilating the of a" should read

--dilating the <u>pupil</u> of a--.

Column 4, Lines 25-26, "P. Arpa, M.D., 12: S89" should read --P. Arpa, M.D., 12:<u>S87</u>-S89--.

Signed and Sealed this

Twenty-eight Day of March, 1995

Attest:

BRUCE LEHMAN

Attesting Officer     Commissioner of Patents and Trademarks